United States Patent [19]

Schlee et al.

[11] 3,962,327

[45] June 8, 1976

[54] PROCESS FOR THE PRODUCTION OF N-HALOFORMYLCARBAMIC ACID HALIDE COMPOUNDS

[75] Inventors: Hans Georg Schlee, Cologne; Klaus Sasse, Schildgen; Engelbert Kuhle, Bergisch, Gladbach, all of Germany

[73] Assignee: Bayer Aktiengesellschaft, Leverkusen, Germany

[22] Filed: Oct. 1, 1974

[21] Appl. No.: 510,971

[30] Foreign Application Priority Data
Oct. 13, 1973 Germany............................ 2351556

[52] U.S. Cl....................... 260/544 C; 260/248 NS; 260/248 R; 260/249.5; 260/455 A; 260/471 C; 260/482 C; 260/543 R
[51] Int. Cl.[2]....................................... C07C 125/03
[58] Field of Search................................. 260/544 C

[56] References Cited
UNITED STATES PATENTS
3,536,756  10/1970  Zumach et al.................. 260/544 C Primary Examiner—Ethel G. Love
Attorney, Agent, or Firm—Burgess, Dinklage & Sprung

[57] ABSTRACT

N-haloformylcarbamic acid halide compounds of the formula

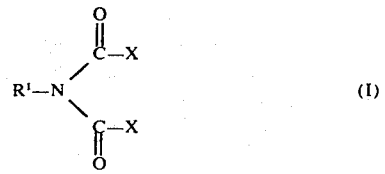

wherein
$R^1$ is an optionally substituted aliphatic, cycloaliphatic, araliphatic or aromatic radical; and
X is a halogen selected from fluorine, chlorine or bromine;

are prepared by a process which comprises reacting an N-haloformylcarbamic acid thio ester of the formula

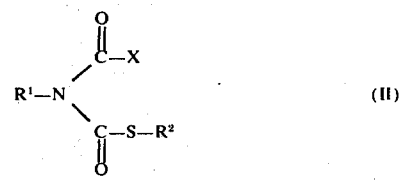

in which
$R^1$ and X are identified as above, and
$R^2$ represents an optionally substituted aliphatic or araliphatic radical, with at least 2 mols of fluorine, chlorine or bromide per thiol ester group at a temperature of −20° to 100°C.

16 Claims, No Drawings

PROCESS FOR THE PRODUCTION OF N-HALOFORMYLCARBAMIC ACID HALIDE COMPOUNDS

The present invention relates to a new process for the preparation of certain N-haloformylcarbamic acid halide compounds. These halide compounds can be employed as intermediates for the preparation of herbicides.

It is known that N-chloroformylcarbamic acid chlorides can be prepared by chlorination of 1,2,4-dithiazolidine-3,5-diones, from *Synthesis,* 1970, pages 542–543 and German Auslegeschrift (German Published Specification) No. 1,298,095. However, this process suffers from various disadvantages. Thus, the use of 1,2,4-dithiazolidine-3,5-diones as starting compounds involves considerable effort, since their preparation — by reaction of formamides or thionocarbamates with chlorocarbonylsulphenyl chloride — is relatively very expensive, can scarcely be carried out on an industrial scale and in some cases the yields are unsatisfactory; furthermore, the chlorination of these compounds may itself also give unsatisfactory yields.

It is also known that N-chloroformylcarbamic acid chlorides can be prepared by addition of phosgene to isocyanates at elevated pressure and high temperatures, from German Offenlegungsschrift (German Published Specification) No. 1,932,830. This process also suffers from various disadvantages. Thus, the use of phosgene at elevated pressure and at the requisite high temperatures entails considerable technical effort. The yields achievable are entirely unsatisfactory. Furthermore, aromatic N-chloroformylcarbamic acid halides cannot be prepared at all by this process.

The process of the instant invention substantially overcomes or obviates these disadvantages of conventional syntheses.

Essentially, the present invention provides a process for the preparation of a N-haloformylcarbamic acid halide of the general formula

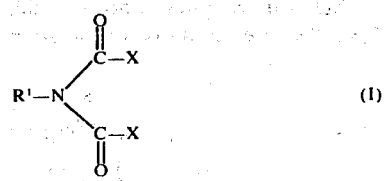

in which
R$^1$ is an optionally substituted aliphatic, cycloaliphatic, araliphatic or aromatic radical; and
X is a halogen selected from fluorine, chlorine or bromine;
which process comprises reacting an N-haloformylcarbamic acid thio ester of the general formula

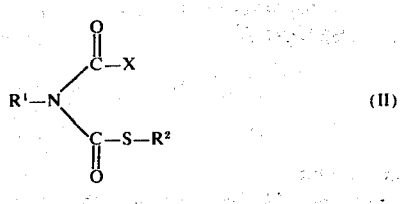

in which
R$^1$ and X are identified as above, and
R$^2$ represents an optionally substituted aliphatic or araliphatic radical,
with at least 2 mols of fluorine, chlorine or bromine per thiol ester group at a temperature of −20° to 100°C.

Preferably, R$^1$ is straight-chain or branched alkyl radical of from 1 – 8 carbon atoms, a cycloalkyl radical of from 5 – 7 carbon atoms, or an aralkyl or aryl radical of from 6 – 10 carbon atoms, which can optionally be substituted by halogen, alkyl and/or haloalkyl, each of from 1 – 4 carbon atoms, and R$^2$ is straight-chain or branched alkyl radical of from 1 – 6 carbon atoms or an aralkyl radical, which can optionally be substituted by alkyl of from 1 to 4 carbon atoms and/or halogen.

The reaction is optionally carried out in the presence of a diluent.

The process according to the invention exhibits various advantages over the known processes. Thus, the N-haloformylcarbamic acid thiol esters used as starting compounds can be prepared much more simply, in higher yield and with substantially greater substitution than, say, 1,2,4-dithiazolidine-3,5-diones, the preparation of which is expensive, and presents problems (because the yields are often low, there are numerous by-products and, in the case of aliphatic substitution, stoichiometric amounts of an auxiliary base are employed).

While the halogenation of 1,2,4-dithiazolidine-3,5-diones only gives by-products which cannot be used further, the alkyl halides which arise in the process according to the invention can, after purification if necessary, be re-introduced into the process of synthesis, say to prepare starting compounds according to the formula (III) (see below). Since the compounds of formula (I) intermediates for the preparation of herbicides, this is a great advantage ecologically and economically, as is the fact that the amount of halogen required is one-third lower.

Since the halogenation temperature can be kept low and catalysis is not required, the apparatus requirements are substantially lower than, say, in the case of the phosgenation of isocyanates under elevated pressure and at elevated temperature. The phosgenation of isocyanates gives a mixture of compounds which is difficult to separate. In the course of the purification processes which are therefore necessary a large part of the reaction product again decomposes. As, in addition, the conversions are frequently low, the reaction thus only gives an extremely low and unsatisfactory overall yield. In contrast, the process according to the invention gives products of high purity with very good conversions, so that purification is in most cases no longer necessary or, if it is necessary, it is very simple and can be carried out virtually without loss.

The process according to the invention also very readily permits the preparation of N-haloformylcarbamic acid halides with aromatic substituents on the nitrogen, which cannot be prepared at all by phosgenation of isocyanates. The process according to the invention thus exhibits surprising advantages and represents a valuable enrichment of the art.

If N-chloroformyl-phenylcarbamic acid methylthiol ester and chlorine are used as starting compounds, the course of the reaction according to the invention is illustrated by the following formula scheme:

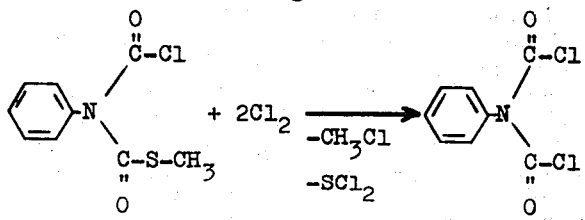

The starting compounds of the formula (II) are not previously known but form the subject of our earlier patent application Ser. No. 416 569, filed Nov. 16, 1973. Such a N-haloformylcarbamic acid thiol ester can be prepared by reacting a compound of the general formula

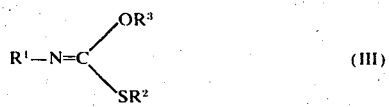

in which
R¹ and R² have the abovementioned meanings and
R³ has the same range of meanings as R²,
with at least an equimolar amount of fluorophosgene, phosgene or bromophosgene at a temperature of −20 to +200°C.

This reaction is optionally carried out in the presence of a diluent, for example a hydrocarbon such as hexane or benzene, a halogenated hydrocarbon such as a chloroform or carbon tetrachloride, or a nitrohydrocarbon, such as nitromethane or nitrobenzene. In general, the procedure followed when carrying out this process is to introduce phosgene into the solution or suspension of the imino compound of formula (III) in an inert solvent, if necessary while cooling, or to introduce the solution or suspension of the imino compound into a solution of phosgene in an inert solvent. The reaction mixture is then brought to the desired reaction temperature depending on the reactivity of the starting compounds used, if appropriate while passing in further phosgene, and after completion of the reaction is worked up in the usual manner, optionally involving distillation. The compounds of formula (II) thus obtained may be purified by distillation, if desired under reduced pressure, and/or by recrystallization (see the Examples below).

The following may be mentioned individually as examples of starting compounds of the formula (II): N-chloroformyl-methylcarbamic acid methylthiol ester, butylthiol ester and benzylthiol ester; N-chloroformyl-propylcarbamic acid methylthiol ester, propylthiol ester and benzylthiol ester; N-chloroformyl-isopropyl-carbamic acid methylthiol ester, butylthiol ester and benzylthiol ester; N-chloroformyl-tert.-butylcarbamic acid methylthiol ester, ethylthiol ester and benzylthiol ester; N-chloroformylsec.-butylcarbamic acid methylthiol ester, butylthiol ester and benzylthiol ester; N-bromoformyl-isobutylcarbamic acid methylthiol ester, ethylthiol ester, butylthiol ester and benzylthiol ester; N-chloroformylcyclohexylcarbamic acid methylthiol ester, butylthiol ester and benzylthiol ester; N-chloroformylphenylcarbamic acid methylthiol ester, butylthiol ester and bencylthiol ester; and N-bromoformyl-4-chlorophenylcarbamic acid methylthiol ester, ethylthiol ester, butylthiol ester and benzylthiol ester.

In the reaction of the compound of formula (II) and the halogen, any inert organic solvent can be used as diluent. Preferred ones include hydrocarbons such as petroleum ether, benzene, toluene and xylene, and chlorinated hydrocarbons, such as methylene chloride, chloroform and carbon tetrachloride.

The reaction temperatures can be varied over a wide range. In general, the reaction is carried out at −20° to 100°C, preferably 0° to 50°C.

The reaction is preferably carried out under normal pressure but can also be carried out under elevated pressure.

In carrying out the process according to the invention, at least 2, generally 2 – 3, mols of fluorine, chlorine or bromine are employed per mol of the compound of formula (II). Gaseous halogens may be introduced, if appropriate while cooling, into a solution or suspension of a compound of the formula (II) in an inert organic solvent; liquid halogens may be added dropwise to such a solution or suspension. The reaction is exothermic.

The reaction product may be isolated in a simple manner by distillative separation of the reaction mixture. Aromatic N-Haloformylcarbamic acid halides are left as a residue and can be purified by recrystallization.

In a particular embodiment of the process according to the invention, the starting compound of the formula (II) need not be employed as such, but can be prepared in situ by reacting a compound of the formula (III) with at least 1 molar equivalent of fluorophosgene, phosgene or bromophosgene, as described above. The reaction mixture thereby produced can subsequently be halogenated direct — without working up — with fluorine, chlorine or bromine, in accordance with the invention.

Some of the N-haloformylcarbamic acid halides of formula (I) which can be prepared according to the invention are known (compare German Patent Specification No. 1,298,095).

The compounds of formula (I) can be used as intermediates for the synthesis of herbicidally active tetrahydro-1,3,5-triazine-2,6-diones. These herbicidal active compounds form the subject of our earlier patent application Ser. No. 407 693, filed Oct. 18, 1973.

Thus, for example, a herbicidally active tetrahydro-1,3,5-triazine-2,6-dione of the general formula

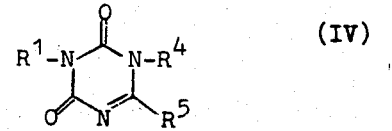

in which
R¹ has the abovementioned meaning,
R⁴ represents hydrogen, amino or alkylideneamino and
R⁵ represents alkyl or alkylthio,
is obtained when a N-haloformyl-carbamic acid halide of the formula (I) is reacted with a compound of the general formula

in which
R⁴ and R⁵ have the abovementioned meanings, or with a salt thereof, in the presence of an acid-binding agent (for example an alkali metal hydroxide such as sodium hydroxide, an alkali metal carbonate such as potassium carbonate or a tertiary amine such as triethylamine or pyridine) and optionally in the presence of a diluent (for example a hydrocarbon such as benzene or an ether such as dioxan) at a temperature of 0° to 50°C, preferably 20° to 40°C; in cases in which $R^4$ represents amino, this functional group can first be protected by hydrazone formation and can easily be liberated again after the reaction (see the preparation Examples and use Examples below; compare also German Offenlegungsschrift (German Published Specification) No. 2,245,449). Many of the compounds of the formula (V) are already known and those which are not known can be prepared according to known processes (compare, for example, Houven-Weyl, Methoden der organischen Chemie (Methods of Organic Chemistry), 4th edition, volume VIII, pages 170–193, volume IX, pages 884–915 and volume XI/2, pages 38–69).

The following Examples 1 to 18 illustrate the process according to the invention (Example 2 illustrate the embodiment in which the compound of formula (II) is prepared in situ).

EXAMPLE I

Preparation of N-chloroformyl-methylcarbamic acid chloride

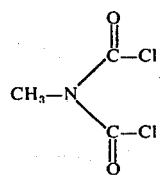

21 g (0.3 mol) of chlorine were passed into a solution of 16.75 g (0.1 mol) of N-chloroformyl-methcarbamic acid methylthiol ester in 100 ml of carbon tetrachloride at 25°C. An exothermic reaction took place and the solution assumed a red-yellow colour. After the end of the reaction, the solvent and the sulphur chlorides produced were removed in a water pump vacuum. The residue was fractionated in a high vacuum. 13.4 g (86%) of N-chloroformyl-methylcarbamic acid chloride were obtained as a pale yellow liquid. Boiling point: 30°–31°C/0.2 mm.

EXAMPLE 2

Preparation of N-Chloroformyl-isopropylcarbamic acid chloride

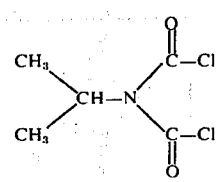

10.9 kg (110 mols) phosgene were passed into a solution of 16.1 kg (100 mols) of isopropylimino-ethyl-methyl-thiolcarbonate in 100 litres of carbon tetrachloride, with some cooling. The solution was briefly flushed with nitrogen and 21 kg (300 mols) of chlorine were then passed in. An exothermic reaction took place and the solution assumed a red-yellow color. After the end of the reaction the solvent and sulphur chlorides produced were removed in a water-pump vacuum and the residue was fractionated. N-chloroformyl-isopropylcarbamic acid chloride was obtained in 89% yield as a red oil. Boiling point: 66°–67°C/12 mm.

EXAMPLE 3

Preparation of N-bromoformyl-methylcarbamic acid bromide

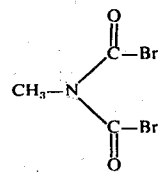

Analogously to Example 1, N-bromoformyl-methylcarbamic acid methylthiol ester and bromine gave N-bromoformyl-methylcarbamic acid bromide, in 81% yield, as a red oil. Boiling point: 67°–69°C/0.3 mm.

EXAMPLES 4 – 18

The following compounds were obtained analogously to Example 1 or 2:

Table 1

| Example | Structural formula | Yield | Boiling point/pressure | Melting point, (°C) |
|---|---|---|---|---|
| 4 | $C_2H_5$—N(C(O)Cl)$_2$ | 81 % | 43–44°/0.1 mm | — |
| 5 | $C_3H_7$—N(C(O)Cl)$_2$ | 84 % | 43–45°/0.2 mm | — |
| 6 | $C_4H_9$—N(C(O)Cl)$_2$ | 87 % | 55–56°/0.1 mm | — |

Table 1-continued

| Example | Structural formula | Yield | Boiling point/pressure | Melting point, (°C) |
|---|---|---|---|---|
| 7 | (CH$_3$)$_2$CH–CH$_2$–N(COCl)$_2$ | 91 % | 51–52°/0.2 mm | — |
| 8 | C$_2$H$_5$–CH(CH$_3$)–N(COCl)$_2$ | 87 % | 39–40°/0.1 mm | — |
| 9 | (CH$_3$)$_3$C–N(COCl)$_2$ | 80 % | 32–33°/0.1 mm | — |
| 10 | C$_6$H$_{11}$–N(COCl)$_2$ | 88 % | 80–82°/0.3 mm | — |
| 11 | C$_6$H$_5$–CH$_2$–N(COCl)$_2$ | 91 % | 96–97°/0.2 mm | — |
| 12 | C$_6$H$_5$–N(COCl)$_2$ | 83 % | — | 61–63 (cyclohexane) |
| 13 | 4-Cl-C$_6$H$_4$–N(COCl)$_2$ | 93 % | — | 106–107 (cyclohexane) |
| 14 | 3,4-Cl$_2$-C$_6$H$_3$–N(COCl)$_2$ | 85 % | — | 101–103 (cyclohexane) |
| 15 | 2,4-Cl$_2$-C$_6$H$_3$–N(COCl)$_2$ | 95 % | — | — |

Table 1-continued

| Example | Structural formula | Yield | Boiling point/pressure | Melting point, (°C) |
|---|---|---|---|---|
| 16 | | 86 % | — | 108–109 (petroleum ether) |
| 17 | | 78 % | — | 65–66 (cyclohexane) |
| 18 | | 82 % | — | 106–108 (petroleum ether) |

The following Examples B-1 to B-4 illustrate the preparation of the starting materials of the formula (II), above:

EXAMPLE B-1

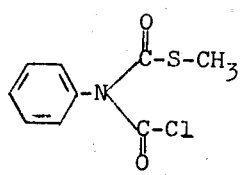

19.5 g (0.1 mol) of phenylimino-ethyl-methylthiol-carbonate were dissolved in 100 ml of methylene chloride. 20 g (0.2 mol) of phosgene were passed in at room temperature, while stirring. The reaction took place exothermically. The solution was stirred for a further 2 hours and evaporated in vacuo. The residue was recrystallized from petroleum ether/xylene (1:1). 18.5 g (81%) of N-chloroformylphenylcarbamic acid methylthiol ester were obtained as a colorless power of melting point: 136°–138°C.

EXAMPLE B-2

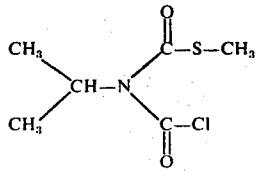

Analogously to Example 1, isopropylimino-ethylmethylthiol-carbonate and phosgene gave N-chloroformyl-isopropylcarbamic acid methylthiol ester, in 91% yield, as a yellow oil which was characterized spectroscopically.

The infrared spectrum showed a double band at 1,670 cm$^{-1}$ and 1.740 cm$^{-1}$. In the nuclear resonance spectrum, the singlet of the methylthiol ester was at 2.33 ppm (in deuterochloroform at 60 MHz).

EXAMPLE B-3

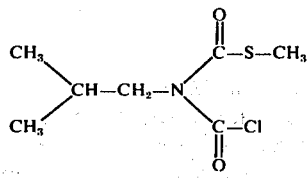

Analogously in Example 1, isobutylimino-ethyl-methylthio-carbonate and phosgene gave N-chloroformyl-isobutylcarbamic acid methylthiol ester, in 50% yield, as a yellow oil. The infrared spectrum showed a double band at 1,670 cm$^{-1}$. The nuclear resonance spectrum in deuterochloroform at 60 MHz showed the singlet of the methylthiol ester at 2.33 ppm.

EXAMPLE B-4

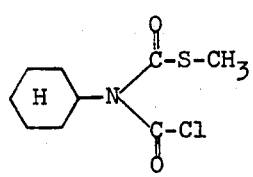

Analogously to Example 1, cyclohexylimino-ethyl-methylthiol-carbonate and phosgene gave N-chloroformylcyclohexylcarbamic acid methylthiol ester, in 89% yield, as a yellow oil.

The following Examples C-1 to C-8 illustrate the preparation of herbicidally active tetrahydro-1,3,5-triazine-2,6-diones of the formula (IV).

EXAMPLE C-1

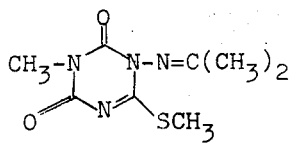

15.6 g (0.1 mol) of N-methyl-bis-(chlorocarbonyl)-amine were dissolved in 100 ml of benzene and the solution was added dropwise, while stirring, to 27.3 g (0.1 mol) of acetone S-methyl-isothio-semicarbazone hydroiodide suspended in 100 ml of benezene. 30.3 g (0.2 mol) of triethylamine in 50 ml of benzene were then slowly added dropwise. The mixture was stirred for a further hour and the precipitate was filtered off. It was introduced into 100 ml of chloroform and 100 ml of water and extracted by shaking. The chloroform phase was separated off, dried over calcium chloride and evaporated in vacuo, together with the benzene filtrate. The residue was recrystallized from isopropanol. 17.3 g (76%) of 1-methyl-3-isopropylideneamino-4-methylmercapto-tetrahydro-1,3,5-triazine-2,6-dione were obtained as a colorless powder of melting point 130°–132°C.

EXAMPLE C-2

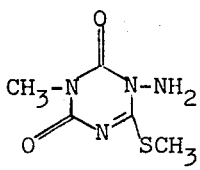

22.8 g (0.1 mol) of 1-methyl-3-isopropylideneamino-4-methylmercapto-tetrahydro-1,3,5-triazine-2,6-dione (prepared according to Example C-1) were dissolved in 250 ml of ethanol and warmed, with addition of a little p-toluene-sulphonic acid, for 5 hours to 50°C, a vacuum of approximately 200 mm Hg being applied. The mixture was evaporated in vacuo and the residue was recrystallized from ethanol. 18 g (96%) of 1-methyl-3-amino-4-methylmercapto-tetrahydro-1,3,5-triazine-2,6-dione were obtained as colorless needles, melting point 174°–175°C.

EXAMPLE C-3

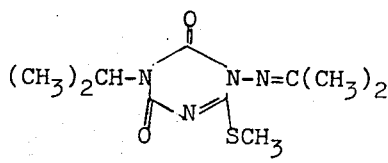

Analogously in Example C-1, N-isopropyl-bis-(chlorocarbonyl)-amine (prepared analogously to Synthesis 1970, page 542–543: boiling point$_{12}$: 66° – 67°C) and acetone S-methylisothio-semicarbazone hydroiodide gave, with addition of triethylamine, 1-isopropyl-3-isopropylideneamino-4-methylmercapto-tetrahydro-1,3,5-triazine-2,6-dione as a pale yellow powder of melting point 110°–112°C.

EXAMPLE C-4

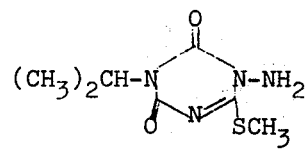

Analogously to Example C-2, 1-isopropyl-3-isopropylindeneamino-4-methylmercapto-tetrahydro-1,3,5-triazine-2,6-dione (prepared according to Example C-3) gave 1-isopropyl-3-amino-4-methylmercapto-1,3,5-triazine-2,6-dione as colorless needles of melting point 148°–150°C.

EXAMPLE C-5

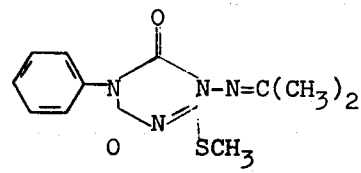

Analogously to Example C-1, N-phenyl-bis-(chlorocarbonyl)-amine and acetone S-methyl-isothiosemicarbazone hudroiodide, with addition of triethylamine, gave 1-phenyl-3-isopropylideneamino-4-methylmercapto-tetrahydro-1,3,5-triazine-2,6-dione as a pale yellow powder of melting point 206°–207°C.

EXAMPLE C-6

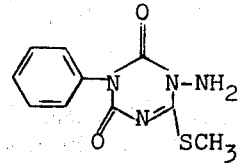

Analogously to Example C-2, 1-phenyl-3-isopropylideneamino-4-methylmercapto-tetrahydro-1,3,5-triazine-2,6-dione (prepared according to Example C-5) gave 1-phenyl-3-amino-4-methylmercapto-tetrahydro-1,3,5-triazine-2,6-dione as colorless needles of melting point 205°–208°C.

EXAMPLE C-7

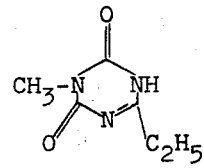

10.9 g (0.1 mol) of propionamidine hydrochloride were suspended in 125 ml of water and 200 ml of benzene. 15.6 g (0.1 mol) of N-methyl-bis-(chlorocarbonyl)-amine in 100 ml of dry benzene and 18 g (0.45 mol) of sodium hydroxide dissolved in 100 ml of water were simultaneously slowly added dropwise from 2 dropping funnels, with vigorous stirring. The reaction took place exothermically. The mixture was stirred for a further hour and the aqueous phase was separated off, acidified with glacial acetic acid and evaporated in vacuo. The residue was repeatedly extracted by boiling with ethyl acetate. The solution was concentrated in vacuo and cooled. The precipitate was filtered off. 7.8 g (50%) of 1-methyl-4-ethyl-tetrahydro-1,3,5-triazine-2,6-dione were obtained as colorless needles of melting point 202°–203°C.

EXAMPLE C-8

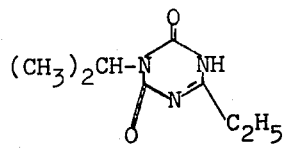

Analogously to Example C-6, propionamidine hydrochloride and N-isopropyl-bis-(chlorocarbonyl)-amine gave 1-isopropyl-4-ethyl-tetrahydro-1,3,5-triazine-2,6-dione as colorless needles of melting point 146°–148°C:

The following Examples D-1 and D-2 illustrate the use of tetrahydro-1,3,5-triazine-2,6-dione of formula (IV), above, as herbicides. The active compounds used in these Examples are identified the the following list.

| List of active compounds | |
|---|---|
| Active compound No. | |
| C-5 | 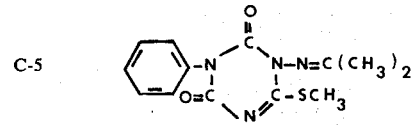 |
| C-6 | 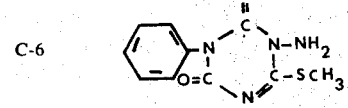 |
| C-3 | 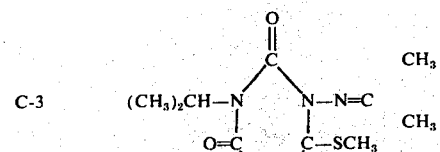 |
| C-8 | 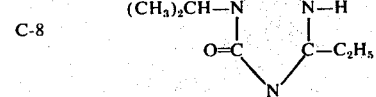 |

| List of active compounds | | |
|---|---|---|
| Active compound No. | | |
| C-4 | 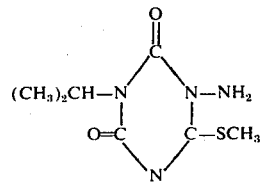 | |
| VM-1 | 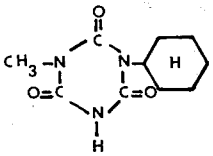 | (known) |
| VM-2 | 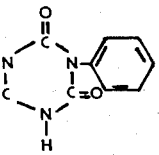 | (known) |

EXAMPLE D-1

Post-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way as to apply the amounts of active compound per unit area which are indicated in Table D-1. Depending on the concentration of the spray liquor, the amount of water used was between 1,000 and 2,000 litres/ha. After three weeks, the degree of damage to the plants was determined and characterized by the values 0 – 5, which had the following meaning:

0 no effect
1 a few slightly burnt spots
2 marked damage to leaves
3 some leaves and parts of stalks partially dead
4 plant partially destroyed
5 plant completely dead The active compounds, the amounts used and the results can be seen from Table D-1.

Table D-1

| Active Compound No. | Amount of active compound used, kg/ha | Post-emergence test | | | | | | | | | |
|---|---|---|---|---|---|---|---|---|---|---|---|
| | | Echino-chloa | Cheno-podium | Sina-pis | Galin-soga | Stell-aria | Matr-caria | Carrots | Oats | Cotton | Wheat | Beans |
| C-3 | 1 | 4–5 | 5 | 5 | 5 | 5 | 5 | 5 | 4–5 | 5 | 5 | 5 |
| | 0.5 | 4 | 5 | 5 | 5 | 4 | 4 | 5 | 4 | 5 | 5 | 4 |
| C-8 | 1 | 4 | 5 | 5 | 4–5 | 5 | 4 | 1 | 3 | 3 | 4 | 4 |
| | 0.5 | 3 | 4 | 5 | 4 | 4–5 | 4 | 0 | 2–3 | 2 | 3 | 3 |
| C-4 | 1 | 5 | 5 | 5 | 5 | 5 | 5 | 5 | 5 | 5 | 5 | 5 |
| VM-1 (known) | 1 | 1 | 0 | 0 | 0 | 0 | 0 | 0 | 0 | 0 | 0 | 1 |
| | 0.5 | 1 | 0 | 0 | 0 | 0 | 0 | 0 | 0 | 0 | 0 | 0 |
| VM-2 (known) | 1 | 2 | 2 | 4 | 0 | 0 | 1 | 0 | 2 | 0 | 0 | 2 |
| | 0.5 | 1 | 1 | 4 | 0 | 0 | 0 | 0 | 2 | 0 | 0 | 2 |

EXAMPLE D-2

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined and characterized by the values 0–5, which had the following meaning:

0 no effect
1 slight damage or delay in growth
2 marked damage or inhibition of growth
3 heavy damage and only deficient development or only 50% emerged
4 plants partially destroyed after germination or only 25% emerged
5 plants completely dead or not emerged.

The active compounds, the amounts applied and the results obtained can be seen from Table D-2.

It will be appreciated that the instant specification and examples are set forth by way of illustration and not limitation, and that various modifications and changes may be made without departing from the spirit and scope of the present invention.

What is claimed is:

1. Process for the preparation of an N-haloformylcarbamic acid halide compound of the formula

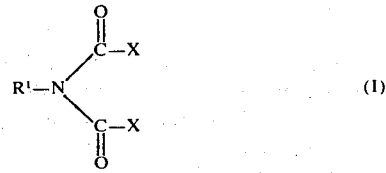

in which
R¹ is substituted alkyl of up to 8 carbon atoms, substituted cycloalkyl of from 5 to 7 ring carbon atoms or substituted aralkyl or aryl of from 6 to 10 carbon atoms in the aryl moiety, wherein the substituents are selected from the group consisting of halogen, alkyl and haloalkyl of from 1 to 4 carbon atoms; and
X is fluorine, chlorine or bromine,
which process comprises reacting an N-haloformylcarbamic acid thiol ester of the formula

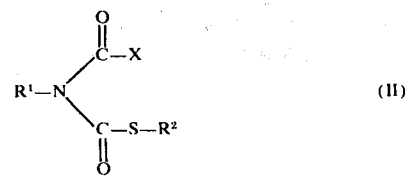

in which
R¹ and X are identified as above, and
R² is straight-chain or branched alkyl of from 1 to 6

Table D-2

| Active compound No. | Amount of active compound used, kg/ha | Pre-emergence test | | | | | | | | | | | |
|---|---|---|---|---|---|---|---|---|---|---|---|---|---|
| | | Echino-chloa | Cheno-podium | Sina-pis | Lol-ium | Stell-aria | Galin-soga | Matri-caria | Avena fatua | Cotton | Wheat | Buck-wheat | Corn |
| C-5 | 5 | 5 | 5 | 5 | 5 | 5 | 5 | 5 | 5 | 5 | 3 | 5 | 3 |
| | 2.5 | 4 | 5 | 4 | 5 | 5 | 5 | 5 | 5 | 5 | 3 | 5 | 2 |
| C-6 | 5 | 5 | 5 | 5 | 5 | 5 | 5 | 5 | 4 | 2 | 3 | 4–5 | 2 |
| | 2.5 | 4 | 5 | 4 | 5 | 5 | 5 | 5 | 3 | 1 | 3 | 3 | 1 |
| C-3 | 5 | 5 | 5 | 5 | 5 | 5 | 5 | 5 | 5 | 4–5 | 3 | 5 | 3 |
| | 2.5 | 5 | 5 | 5 | 5 | 5 | 5 | 5 | 5 | 4 | 3 | 4–5 | 2 |
| C-4 | 5 | 5 | 5 | 5 | 5 | 5 | 5 | 4–5 | 5 | 5 | 4–5 | 2 | |
| | 2.5 | 5 | 5 | 4–5 | 5 | 5 | 5 | 5 | 4 | 4 | 4 | 4 | 1 |
| VM-1 (known) | 5 | 0 | 0 | 0 | 0 | 0 | 0 | 0 | 0 | 0 | 0 | 0 | 0 |
| | 2.5 | 0 | 0 | 0 | 0 | 0 | 0 | 0 | 0 | 0 | 0 | 0 | 0 |
| VM-2 (known) | | 1 | 0 | 2 | 0 | 1 | 4 | 4 | 1 | 0 | 0 | 2 | 1 |
| | | 0 | 0 | 0 | 0 | 0 | 3 | 2 | 0 | 0 | 0 | 1 | 0 | carbon atoms, aralkyl of from 6 to 10 carbon atoms or substituted aralkyl of from 6 to 10 carbon atoms wherein the substituent is selected from alkyl of up to 4 carbon atoms and halogen,
with at least 2 moles of fluorine, chlorine or bromine per thiol ester group at a temperature of −20° to 100°C.

2. Process as claimed in claim 1 wherein $R^1$ is straight-chain or branched alkyl of from 1 to 8 carbon atoms, cycloalkyl of from 5 to 7 ring carbon atoms, or aralkyl or aryl of from 6 to 10 carbon atoms in the aryl moiety.

3. Process as claimed in claim 1 wherein $R^1$ is substituted alkyl of up to 8 carbon atoms.

4. Process as claimed in claim 1 wherein $R^2$ is straight-chain or branched alkyl of from 1 to 6 carbon atoms.

5. Process as claimed in claim 1 wherein the reaction is carried out in the presence of an inert organic solvent.

6. Process as claimed in claim 5 wherein the inert organic solvent is a hydrocarbon or a chlorinated hydrocarbon.

7. Process as claimed in claim 1 wherein the reaction is carried out at a temperature of from 0° to 50°C.

8. Process as claimed in claim 1 wherein the thiol ester of formula (II) is prepared in situ by reacting a compound of the formula

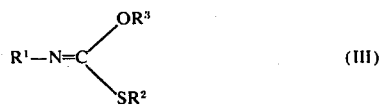

wherein
$R^1$ and $R^2$ are identified as in claim 1 and
$R^3$ is defined as $R^2$ is defined
with at least an equimolar amount of fluorophosgene, phosgene, or bromophosgene at a temperature of −20° to +200°C.

9. Process as claimed in claim 8 wherein the reaction of said compound of formula (III) is carried out in the presence of an inert organic solvent.

10. Process as claimed in claim 9 wherein the inert organic solvent is a hydrocarbon, a halogenated hydrocarbon or a nitrohydrocarbon.

11. Process as claimed in claim 1 wherein N-chloroformyl-methylcarbamic acid chloride is prepared by reacting N-chloroformyl-methylcarbamic acid methylthiol ester with chlorine and recovering the desired compound.

12. Process as claimed in claim 1 wherein N-chloroformyl-sec.-butyl carbamic acid chloride is prepared by reacting N-chloroformyl-sec.-butyl carbamic acid methylthiol ester with chlorine and recovering the desired compound.

13. Process as claimed in claim 1 wherein N-chloroformyl-tert.-butyl carbamic acid chloride is prepared by reacting N-chloroformyl-tert.-butyl carbamic acid methylthiol ester with chlorine and recovering the desired compound.

14. Process as claimed in claim 1 wherein N-chloroformyl-cyclohexyl carbamic acid chloride is prepared by reacting N-chloroformyl-cyclohexyl carbamic acid methylthiol ester with chlorine and recovering the desired compound.

15. Process as claimed in claim 1 wherein N-chloroformyl-phenylcarbamic acid chloride is prepared by reacting N-chloroformyl-phenylcarbamic acid methylthiol ester with chlorine and recovering the desired compound.

16. Process as claimed in claim 1 wherein N-chloroformyl-3,4-dichlorophenyl carbamic acid chloride is prepared by reacting N-chloroformyl-3,4-dichlorophenyl carbamic acid methylthiol ester with chlorine and recovering the desired compound.

* * * * *